US010831865B2

(12) United States Patent
Van De Craen (10) Patent No.: US 10,831,865 B2
(45) Date of Patent: Nov. 10, 2020

(54) MEDICATION MANAGEMENT DEVICE AND METHOD

(71) Applicant: KONINKLIJKE PHILIPS N.V., Eindhoven (NL)

(72) Inventor: Dieter Maria Alfons Van De Craen, Balen (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 288 days.

(21) Appl. No.: 14/406,647

(22) PCT Filed: Jul. 3, 2013

(86) PCT No.: PCT/IB2013/055453
§ 371 (c)(1),
(2) Date: Dec. 9, 2014

(87) PCT Pub. No.: WO2014/006580
PCT Pub. Date: Jan. 9, 2014

(65) Prior Publication Data
US 2015/0161341 A1    Jun. 11, 2015

Related U.S. Application Data

(60) Provisional application No. 61/668,055, filed on Jul. 5, 2012.

(51) Int. Cl.
*G06F 19/00*    (2018.01)
*G06K 9/18*    (2006.01)
(Continued)

(52) U.S. Cl.
CPC ...... *G06F 19/3418* (2013.01); *G06F 19/3456* (2013.01); *G06K 9/18* (2013.01);
(Continued)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS 5,646,912 A    7/1997   Cousin
6,018,289 A    1/2000   Sekura et al.
(Continued)

FOREIGN PATENT DOCUMENTS

JP    2003296454 A    10/2003
JP    2006172261 A1    6/2006
(Continued)

OTHER PUBLICATIONS

Hartl, "Computer-Vision Based Pharmaceutical Pill Recognition on Mobile Phones", Proceedings of CESCG, 14th Central European Seminar on Computer Graphics, 2010, pp. 108.
(Continued)

*Primary Examiner* — Michael Tomaszewski
*Assistant Examiner* — William T. Monticello (57) ABSTRACT

The present invention relates to a medication management device and a corresponding medication management method. The proposed device comprises an imaging unit (12) for capturing images of a medication (1), a medication identification unit (14) for identifying said medication (1) by use of one or more captured images including said medication (16) based on a medication database, and a display (16) for displaying in real time captured images of said medication and overlaid medication information about said medication including medication identification information obtained by said medication identification unit (14).

20 Claims, 6 Drawing Sheets

(51) Int. Cl.
*H04N 5/445* (2011.01)
*H04N 7/18* (2006.01)

(52) U.S. Cl.
CPC ............ *H04N 5/445* (2013.01); *H04N 7/183* (2013.01); *G06F 19/321* (2013.01); *G06F 19/326* (2013.01)

(58) Field of Classification Search
CPC ........ G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 80/00
See application file for complete search history.

(56) References Cited

U.S. PATENT DOCUMENTS

| | | | |
|---|---|---|---|
| 6,028,289 A * | 2/2000 | Robichaud et al. | |
| 6,198,383 B1 | 3/2001 | Sekura et al. | |
| 6,535,637 B1 * | 3/2003 | Wootton et al. | |
| 2007/0185615 A1 * | 8/2007 | Bossi et al. | |
| 2008/0056556 A1 | 3/2008 | Eller et al. | |
| 2010/0042430 A1 * | 2/2010 | Bartfeld | |
| 2011/0246221 A1 | 10/2011 | Camp et al. | |
| 2012/0330684 A1 * | 12/2012 | Jacobs et al. | |
| 2013/0218588 A1 * | 8/2013 | Kehr et al. | |
| 2013/0279774 A1 * | 10/2013 | Helgason et al. | |

FOREIGN PATENT DOCUMENTS

| | | | | |
|---|---|---|---|---|
| JP | 2010225019 A | 10/2010 | | |
| JP | 2011253324 A | 12/2011 | | |
| WO | 0225568 A1 | 3/2002 | | |
| WO | 2011112606 A1 | 9/2011 | | |
| WO | WO2012056317 | * | 5/2012 | ............... G06K 9/20 |
| WO | 2012056499 A1 | 2/2014 | | |

OTHER PUBLICATIONS

Felzenszwalb et al, "Efficient Graph-Based Image Segmentation", Journal of Computer Vision, vol. 59, No. 2, 2004, pp. 1-26.
Matas et al, "Robust Wide Baseline Stereo From Maximally Stable Extremal Regions", British Machine Vision Conference, vol. 1, 2002, p. 384-393.
Koschan et al, "Detectiona ND Classification of Edges in Color Images", IEEE Signal LProcessing Magazine, Jan. 2005, pp. 64-73.
Christoudias et al, "Synergism in Low Level Vision", Int. Conference on Pattern Recognition (ICPR), 2002, 6 Pages.
Hartl et al, "Instant Medical Pill Recognition on Mobile Phones", Proceedings of the IASTED International Conference on Computer Vision, 2011, pp. 188-195.

* cited by examiner

MEDICATION MANAGEMENT DEVICE AND METHOD

CROSS-REFERENCE TO PRIOR APPLICATIONS

This application is the U.S. National Phase application under 35 U.S.C. § 371 of International Application No. PCT/IB2013/055453, filed on Jul. 3, 2013, which claims the benefit of U.S. Provisional Patent Application No. 61/668, 055, filed on Jul. 5, 2012. These applications are hereby incorporated by reference herein.

FIELD OF THE INVENTION

The present invention relates to a medication management device and a corresponding medication management method as well as a computer program for implementing said medication management method on a computer.

BACKGROUND OF THE INVENTION

Medication non-compliance is widely recognized as a major medical problem and different improvements have already been proposed. Some of these solutions aim to improve medication adherence via the use of (smart) pill boxes or dispensers. Pill boxes have evolved from basic containers to "smart" pillboxes providing extra functionality such as lighting up of the specific compartment when it is time to take the particular medication contained in that compartment, and auditory prompts when the cup is not removed from the compartment within an assigned timeframe. Additional prompt options include automatic phone calls, text messages or e-mails. At the end of each week, or month, reports are available online or by email detailing the pillbox activity.

Further, pill dispensers, such as the Philips Medication Dispenser, are known which make it possible for caregivers to prepare and set up medication a week or more in advance. The dispenser signals the patient with audible voice prompts when it is time to take the scheduled medication. If the patient misses a dose or there is a problem with the system, the dispenser automatically places an alert call to the caregiver. Further, the status of the system is checked automatically and a report on the status is available online.

U.S. Pat. No. 6,535,637 describes a dispenser system for filling a pharmaceutical prescription for medications. It includes automatic verification of the type of medication dispensed as part of a filling operation performed by the system. This verification is done using an image processing technique.

U.S. Pat. Nos. 6,018,289 and 6,198,383 describe a device which aids patients in complying with instructions given by a physician for taking prescription medication. The device reminds a patient when the next dose of medication needs to be taken and indicates whether a specified dose has been taken and includes a remote programming feature via a wireless link.

*Computer-Vision based Pharmaceutical Pill Recognition on Mobile Phones*, Hartl, A. et al., 2010. Proceedings of CESCG 2010: The 14th Central European Seminar on Computer Graphics describes a system which simplifies the task of identifying pharmaceutical pills. The pills are identified based on a single input image of pills on a special marker. Estimates for the pill's properties size, shape and color deliver parameters that are used for querying an online pill database. The system is prototyped on a mobile phone.

There are medication management services such as Nex-Dose. The patient receives a small, self-contained, mini-computer that will help him to take medication properly. The device will sound an alarm when it is time to take a medication, and display its name. The care provider can remotely program the NexDose device and review the patient's compliance data that is stored within the device.

Finally, the project Smart Pill Box, e.g. currently described at http://processors.wiki.ti.com/index.php/Project_Smart_Pill_Box, aims to deliver a visual verification system that will keep reminding patients to take their medications until they provide visual proof of taking the pills out of the box and lifting them up to their mouths to ingest. The system uses a low-cost computer and webcam that detects the face of a user and then attempts to track a hand as it moves towards the user's mouth. This action is considered as the taking of the pill. The software will also notify a user if he has taken his pills already for the day. In order to do hand-tracking, the software currently tracks a colored dot on the back of the user's hand in order to accomplish a primitive form of hand-tracking.

Both the pill boxes and dispensers are assumed to be filled correctly each week/month by either the patient or a caretaker. This inhibits changes to the medication or doses without a physical intervention of the patient or a caretaker. For example, in case the filling process is done by the pharmacist, one needs to return the unit when the medication changes. Moreover, this filling process can be error prone. In these systems, there is no verification step that ensures the correctness at the moment when the medication is taken. Further, larger and higher capacity pill dispensers are not suitable for use when away from the home. These units need to be placed in a central location and be easily noticeable to avoid missing medication intakes. Pill boxes that contain medication for multiple days do not fit in pockets and are not very suited for being carried in a pocket.

Smaller portable pill organizers that can be put in a pocket and use vibration to remind the user at pill times exist. However these do not solve the previously mentioned disadvantages and typically can only contain medication for a very limited number of days. Some medications need to be stored in air tight containers, inside a fridge while other types are unsuitable to be stored in a fridge. The containers of these devices however do not allow multiple storage locations.

A medication service such as NexDose uses a mobile device that alerts a user to take a medication by sounding an alarm and displaying the name of the medication. While this approach allows the medication regimen to be easily adapted, it still does not contain a verification step that ensures the correctness at the moment when the medication is taken. Finally, current solutions often fail to take the patient safety into consideration. It is well known that multiple medications also result in adverse drug reactions, heavy side effects, and unwanted interaction effects.

SUMMARY OF THE INVENTION

It is an object of the present invention to provide an improved medication management device and a corresponding medication management method as well as a computer program that provide as many functions of known solutions as possible, provide easy handling for a user and particularly provide sufficient safety against the taking of wrong medication by the user.

In a first aspect of the present invention a medication management device is presented comprising an imaging unit for capturing images of a medication, a medication identification unit for identifying said medication by use of one or more captured images of said medication based on a medication database, and a display for displaying in real time captured images including said medication and overlaid medication information about said medication including medication identification information obtained by said medication identification unit.

In a further aspect of the present invention a corresponding medication management method is presented.

In yet another aspect of the present invention, there is provided a computer program which comprises program code means for causing a computer to perform the steps of the medication management method when said computer program is carried out on a computer or other programmable entity.

Preferred embodiments of the invention are defined in the dependent claims. It shall be understood that the claimed method and computer program have similar and/or identical preferred embodiments as the claimed device and as defined in the dependent claims.

The present invention thus provides a solution that identifies the medication based on a video or image input and a database that contains the properties of medications. Feedback is provided by augmenting the captured image data, preferably video data, showing the medication in its real environment in which it is captured by the image data, with information on the detected medication and discrepancies. This feedback can be extended to display, among others, discovered drug interactions. Thus, a mediated reality component is created by using the captured images and in real-time overlaying feedback to the user, e.g. a patient or care-giver. In contrast, the known solutions use a single image which is static and provide feedback as, for example, text on a display. The advantage of the proposed solution is that the end-user (e.g. a patient) views a live view of the medication which is augmented by the feedback and additional information including at least medication indication information.

This provides the ability to image one or more medications at the same time. Further, in an embodiment it is possible to sweep over different medications that are, e.g., lying on the table in front of the user to search for a particular medication which should be taken.

As mentioned above, according to an embodiment said imaging unit is configured to capture video data of a medication and wherein said display is configured to display said captured video data in real time. This provides immediate and illustrative feedback to the user.

Further, according to an embodiment said medication identification unit is configured to identify characteristic features, in particular size, color, shape, logo and/or inscription, of the medication and for identifying the medication based on said identified characteristic features and said medication database containing a plurality of medications, their characteristic features and medication description, in particular active components, interactions, side effects and intake information.

Said medication database may be stored in the medication management device in a medication database storage for storing said medication database. Alternatively or in addition (e.g. some of the medications) may be stored externally, in which case the device preferably comprises an interface for contacting one or more externally stored medication databases, in particular via a computer network or a communications network.

Preferably, said device comprises a medication intake information unit for obtaining medication intake information based on the medication identification information and a medication intake scheme specifying which medication shall be taken at which point in time, wherein said display is configured to display said medication intake information as part of said overlaid medication information. Thus, the proposed device and method can evaluate a medication intake scheme that specifies which medication needs to be taken at which point in time to determine if it is the right medication that is currently detected or if there is any discrepancy between the medication that should be taken and the medication that is detected.

Said medication intake scheme may be stored in the medication management device in a medication intake scheme storage for storing said medication intake scheme. Alternatively or in addition (e.g. some of the intake schemes) may be stored externally, in which case the device preferably comprises an interface for contacting an externally stored medication intake scheme, in particular from a health record or a medication management service via a computer network or a communications network.

As mentioned, in an embodiment said medication intake information unit is configured to obtain, as part of said medication intake information, information about discrepancies between the identified medication and the medication intake scheme and/or the correct or wrong amount and/or possible interactions between the identified medication and medication contained in the medication intake scheme or previously identified medication.

Further, preferably said medication intake information unit is configured to obtain, as part of said medication intake information, information about missing medication and wherein said display is configured to display a visual or textual representation of said missing medication.

In an embodiment said display is configured to display said overlaid medication information as text or color indication (e.g. a color code indicating that it is the correct or a wrong medication) overlaid to the displayed image and/or to display a link or button for use by a user to obtain additional information about the displayed medication. For instance, by use of such a link a connection to the internet could be opened to search for additional information or to a certain website providing such additional information. In another embodiment the link may be used to establish a connection with the (internal or external) medication database.

In another embodiment the medication management device further comprises a segmentation unit for segmenting captured images and recognizing a medication. This enables an improved medication recognition and identification even if several drugs and/or other items are visible in the captured images.

The proposed medication management device can be implemented as a separate device particularly manufactured for this purpose. However, the proposed medication management device may alternatively be a smart phone, tablet PC, handheld PC, laptop, PDA, augmented reality glasses or augmented reality lenses, which is/are adapted for the desired purpose.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
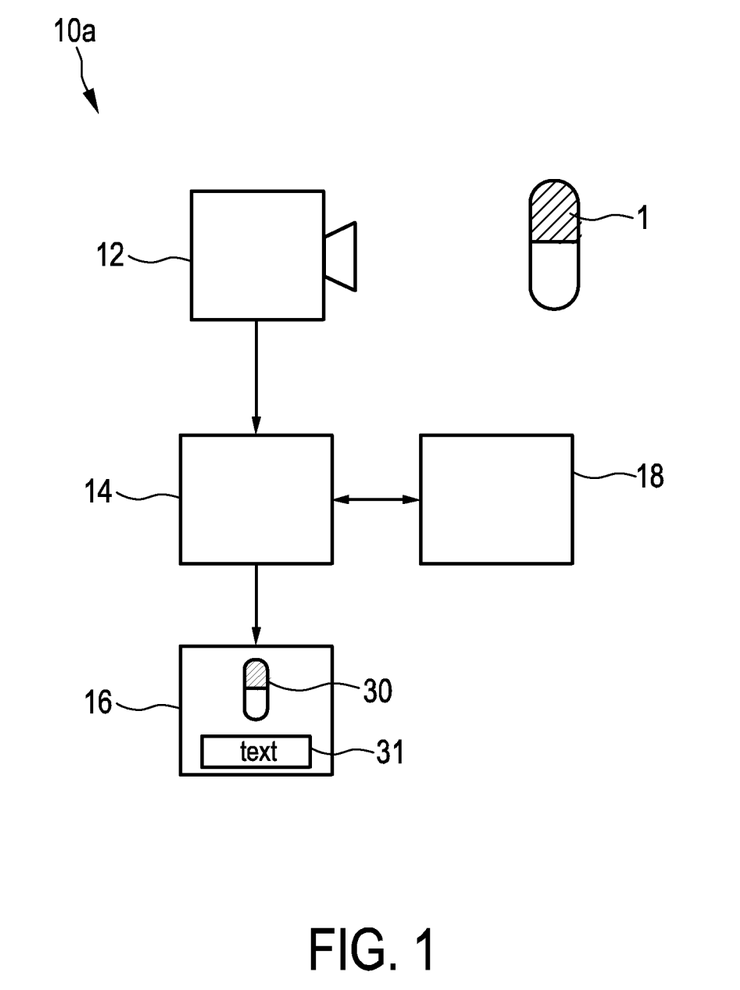
FIG. 1 shows a first embodiment of a medication management device according to the present invention.

FIG. 1 shows a first embodiment of a medication management device 10a according to the present invention. It comprises an imaging unit 12 for capturing images of a medication 1, a medication identification unit 14 for identifying said medication 1 by use of one or more captured images of said medication 1 based on a medication database, and a display 16 for displaying in real time captured images 30 of said medication 1 and overlaid medication information 31 about said medication 1 including medication identification information obtained by said medication identification unit 14. In this embodiment the medication database is stored in a medication database storage 18.

Figure 2:
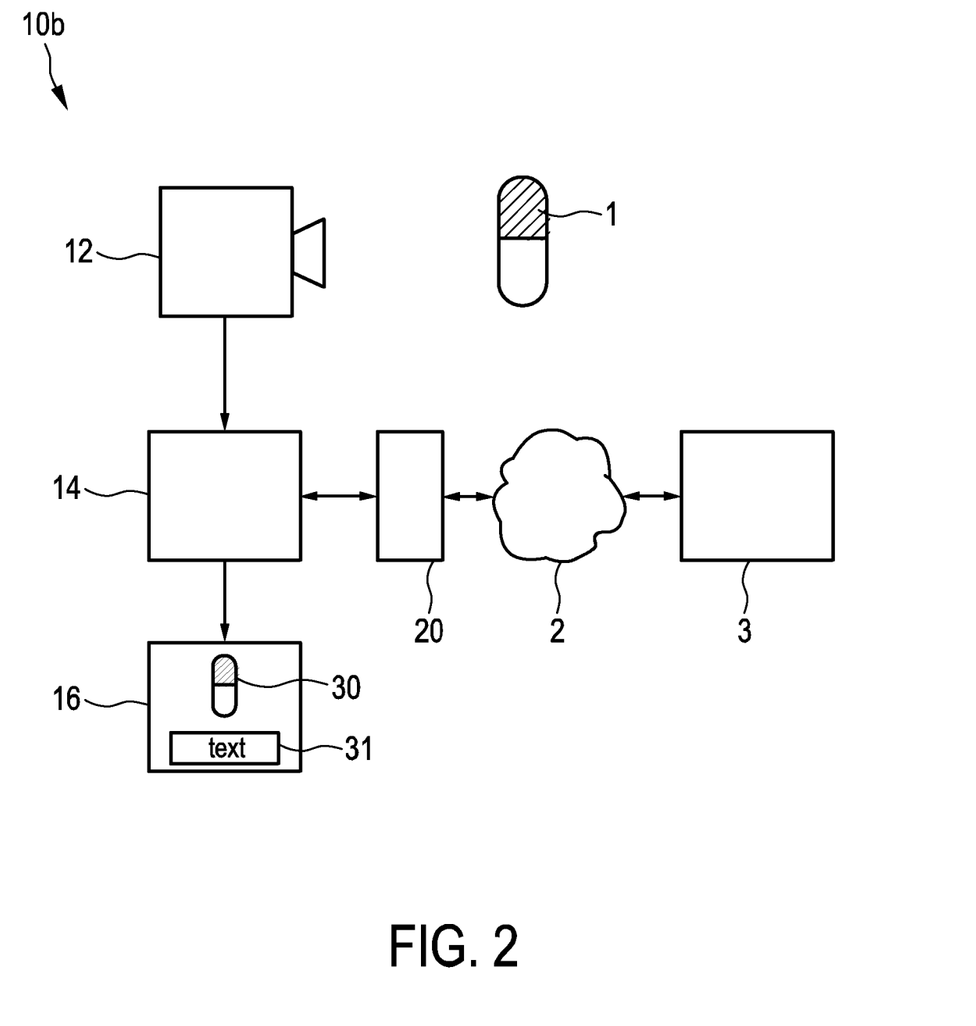
FIG. 2 shows a second embodiment of a medication management device according to the present invention.

FIG. 2 shows a second embodiment of a medication management device 10b according to the present invention. Compared to the first embodiment of the medication management device 10a an interface 20 is provided for contacting one or more externally stored medication databases 3, in particular via a network 2 such as a computer network or a communications network.

In still another embodiment (not shown) both internally and externally a medication database is stored and can be accessed by the medication management device. For instance, information on often used medication can be stored in an internal medication database, whereas information on more unusual medication is stored in one or more external medication database(s).

For identification of medication known algorithms are generally employed. In an embodiment the method described in the above cited document of Hartl A. et al. is used according to which pills are identified based on a single input image of pills on a special marker. Alternatively, other more advanced identification methods may be employed for detection of one or more pills (preferably at the same time from a single image frame), preferably including a step of segmentation as mentioned below. Estimates for the pill's properties such as size, shape and color deliver parameters that are used for querying the medication database. This medication database contains an extensive list of medications with their properties. The information on each medication includes the properties such as size, shape, color and logo but also other information such as a description, interactions and side effects. In practice, this information can be retrieved from multiple online or local sources but for simplicity it is considered here that all data be present in a single source.

Figure 3:
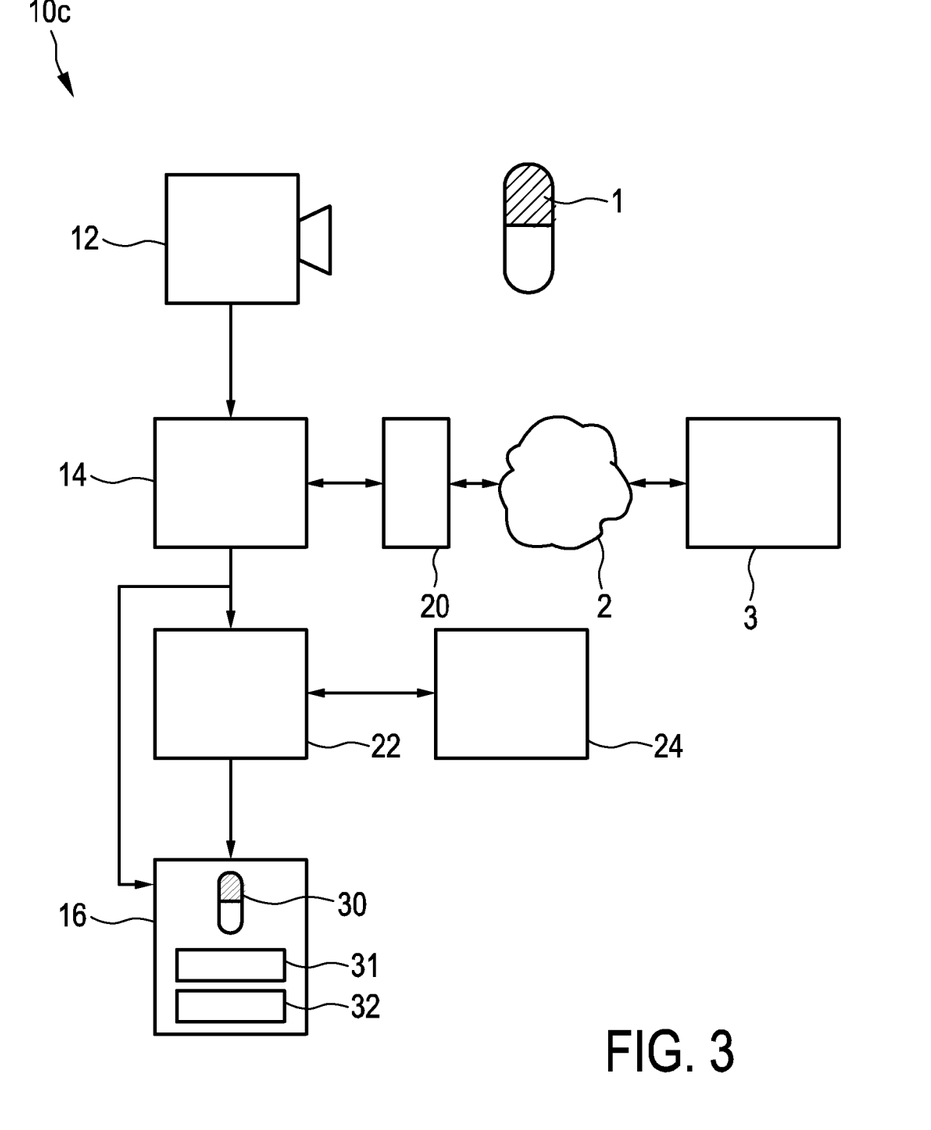
FIG. 3 shows a third embodiment of a medication management device according to the present invention.

FIG. 3 shows a third embodiment of a medication management device 10c according to the present invention. Compared to the second embodiment of the medication management device 10b an additional medication intake information unit 22 is provided for obtaining medication intake information based on the medication identification information and a medication intake scheme specifying which medication shall be taken at which point in time. Said medication intake scheme is stored in this embodiment on an internal medication intake scheme storage 24.

Figure 4:
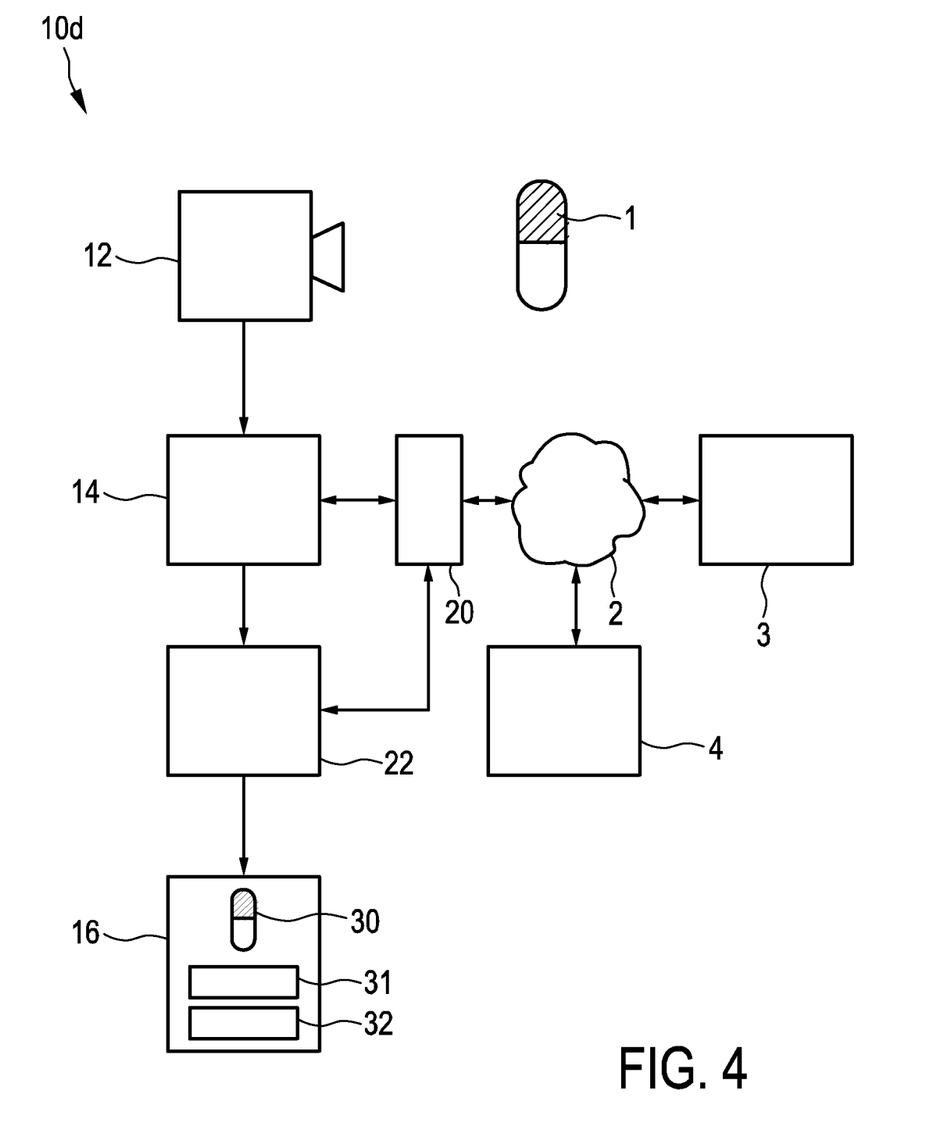
FIG. 4 shows a fourth embodiment of a medication management device according to the present invention.

In a fourth embodiment of the medication management device 10d according to the present invention shown in FIG. 4 the interface 20 is used for contacting one or more externally stored medication databases 4, in particular via the network 2 such as a computer network or a communications network.

In the third and forth embodiments the display 16 is configured to display said medication intake information 32 as part of said overlaid medication information in addition to the image 30 of the medication, in particular the complete video input showing the medication in its real environment, and the medication identification information 31.

Once the presented medication is determined, this set is compared against the user's medication schedule (also called medication intake scheme herein). This medication intake scheme specifies which medication needs to be taken at which point in time. The scheme can be retrieved from a source such as a personal health record or a medication management service or can be stored and available from any internal/external database. As the medication intake schedule is used at time of intake to determine the correctness, updates to the schedule that have occurred just before the intake will still be taken into account.

The applicable set of medication is extracted from the schedule information based on the current time and compared against the determined set of medications. As a result, there can be medications that are missing, superfluous or correct (with respect to both type and quantity). The result of this comparison is used as input to the display for providing appropriate feedback to the user.

To allow the system to operate in both online and offline mode it is possible to store and synchronize necessary (or even all) parts of the information sources locally. This information includes the medication information on medication that is part of the schedule and the actual schedule.

Figure 5:
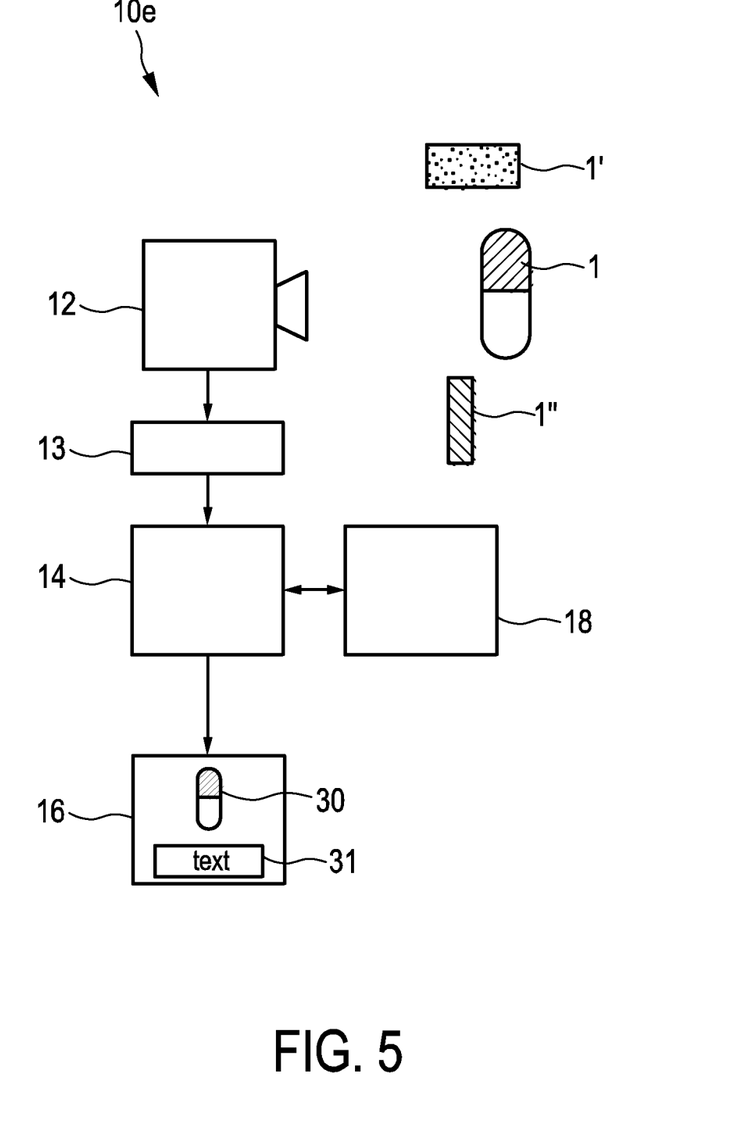
FIG. 5 shows a fifth embodiment of a medication management device according to the present invention.

FIG. 5 shows a fifth embodiment of a medication management device 10e according to the present invention. Compared to the first embodiment of the medication management device 10a a segmentation unit 13 is provided for segmenting captured images and recognizing a medication. For this segmentation a known algorithm as generally used in image processing is preferably used. This segmentation provides to recognize the medication 1 within captured images although several other items (e.g. other medications 1', 1") are visible in the scene captured by the imaging unit 12.

There are several algorithms known for segmentation. Examples are Graph Cuts (P. Felzenszwalb and D. Huttenlocher. Efficient Graph-Based Image Segmentation. In Int. Journal of Computer Vision (IJCV), volume 59(2), 2004.), MSER (J. Matas, O. Chum, M. Urban, and T. Pajdla. Robust Wide Baseline Stereo from Maximally Stable Extremal Regions. In British Machine Vision Conference (BMVC), volume 1, pages 384-393, 2002), Color Canny Edge Detector (A. Koschan and M. Abidi. Detection and Classification of Edges in Color Images. In Signal Processing Magazine (Special Issue on Color Image Processing), volume 22(1), pages 64-73, 2005) and Mean Shift (C. M. Christoudias, B. Georgescu, and P. Meer. Synergism in Low Level Vision. In Int. Conference on Pattern Recognition (ICPR), pages 150-156, 2002).

Figure 6:
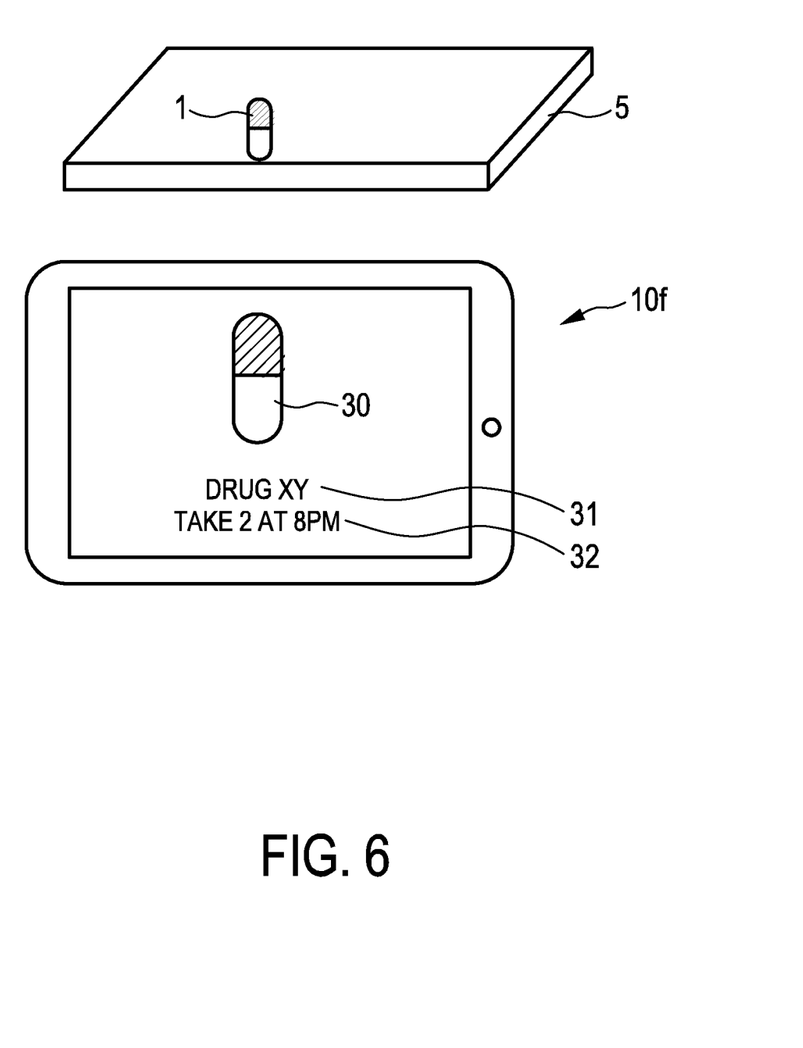
FIG. 6 shows a sixth embodiment of a medication management device according to the present invention.

FIG. 6 shows a practical implementation as a sixth embodiment of a medication management device 10f according to the present invention. The device 10f is embodied as a tablet having a built-in camera that captures images of (one or more) medication 1 that is e.g. put on a table top 5.

In summary, the mediated reality component provided according to the present invention adds information to the user's perception of his medication in its real environment via a device such as a smart phone or tablet. The latter acts as a visual filter between the actual medication and what the user perceives. The results of the comparison between the detected medication and medication scheme are hence added to the user's perception. For one or more, preferably each, of the detected medications, it will indicate whether the medication needs to be taken or not and the reason (e.g. ok, not in schedule, interactions or too many). The location of the medication on the display is known from a preferably provided object segmentation component. Besides the detected medications, missing medications are also displayed in a preferred embodiment. The added information can be further extended by displaying the information known about the medication from the medication database (or providing the option to access this information) and detected medication interactions.

The invention can be applied in the area of medication management and is especially interesting for patients that require multiple medications. It can be used as an extension of or be an integral part of a medication management service. As the component can be run or be part of an application that is run on a device such as a smart phone or tablet, it allows the introduction of a verification step of the correctness of medication intake and provide real-time feedback at the place and time of intake. This invention can be integrated within a medication management service and can be extended to provide its results as input to, for example, alert the caregiver when discrepancies are detected, or create overview reports on the medication intake results.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medication management device, comprising:
an imaging unit for capturing images of a medication;
a medication identification unit configured to identify if the medication is the correct medication for intake by identifying said medication by use of one or more captured images of said medication based on a medication database, the medication identification unit configured to identify said medication by identifying characteristic features of said medication from the one or more captured images and comparing said characteristic features to information about medications contained in the medication database; and
a display for displaying in real time live captured images including said medication and overlaid medication information about said medication including medication identification information obtained by said medication identification unit, wherein said medication management device is one taken from a list of a smart phone, tablet PC, handheld PC, laptop, PDA, augmented reality glasses or augmented reality lenses.

2. The medication management device of claim 1, wherein said imaging unit is configured to capture video data of a medication and wherein said display is configured to display said captured video data in real time.

3. The medication management device of claim 1, wherein the characteristic features include one or any combination of size, color, shape, logo or inscription, and wherein the medication identification unit is further configured to compare said characteristic features to the information for a plurality of medications, the information including characteristic features and medication description, in particular active components, interactions, side effects and intake information, of the plurality of medications.

4. The medication management device of claim 1, further comprising a medication database storage for storing said medication database.

5. The medication management device of claim 1, further comprising an interface for contacting one or more externally stored medication databases, in particular via a network such as a computer network or a communications network.

6. The medication management device of claim 1, further comprising a medication intake information unit for obtaining medication intake information based on the medication identification information and a medication intake scheme specifying which medication shall be taken at which point in time,
wherein said display is configured to display said medication intake information as part of said overlaid medication information.

7. The medication management device of claim 6, further comprising a medication intake scheme storage for storing said medication intake scheme.

8. The medication management device of claim 6, further comprising an interface for contacting an externally stored medication intake scheme, in particular from a health record or a medication management service via a computer network or a communications network.

9. The medication management device of claim 6, wherein said medication intake information unit is configured to obtain, as part of said medication intake information, information about discrepancies between the identified medication and the medication intake scheme and/or possible interactions between the identified medication and medication contained in the medication intake scheme or previously identified medication.

10. The medication management device of claim 6, wherein said medication intake information unit is configured to obtain, as part of said medication intake information, information about missing medication and/or the correct or wrong amount and wherein said display is configured to display a visual or textual representation of said missing medication.

11. The medication management device of claim 1, wherein said display is configured to display said overlaid medication information as text or color indication overlaid to the displayed image and/or to display a link or button for use by a user to obtain additional information about the displayed medication.

12. The medication management device of claim 1, further comprising a segmentation unit for segmenting captured images and recognizing a medication.

13. A medication management method, comprising:
capturing images of a medication;
identifying if the medication is the correct medication for intake by identifying said medication by use of one or more captured images including said medication based on a medication database, wherein identifying the medication comprises identifying characteristic features of said medication from the one or more captured images and comparing said characteristic features to information about medications contained in the medication database; and
displaying in real time live captured images of said medication and overlaid medication information about said medication including medication identification information obtained by said medication identification,
wherein said medication management method is carried out by a medication management device, which is one taken from a list of a smart phone, tablet PC, handheld PC, laptop, PDA, augmented reality glasses or augmented reality lenses.

14. A non-transitory computer readable medium encoded with a computer program comprising program code for causing a computer, when the program code is executed by the computer, to perform the following steps:
capturing images of a medication;
identifying if the medication is the correct medication for intake by identifying said medication by use of one or more captured images including said medication based on a medication database, wherein identifying the medication comprises identifying characteristic features of said medication from the one or more captured images and comparing said characteristic features to information about medications contained in the medication database; and
displaying in real time live captured images of said medication and overlaid medication information about said medication including medication identification information obtained by said medication identification,
wherein said medication management method is carried out by a medication management device, which is one taken from a list of a smart phone, tablet PC, handheld PC, laptop, PDA, augmented reality glasses or augmented reality lenses.

15. A medication management device, comprising:
an imaging unit for capturing images of a medication;
a medication identification unit configured to identify if the medication is the correct medication for intake by identifying said medication by use of one or more captured images of said medication based on a medication database, wherein identifying the medication comprises identifying characteristic features of said medication from the one or more captured images and comparing said characteristic features to information about medications contained in the medication database; and
a display for displaying in real time captured images including said medication and overlaid medication information about said medication including medication identification information obtained by said medication identification unit,
wherein said medication management device is one taken from a list of a smart phone, tablet PC, handheld PC, laptop, PDA, augmented reality glasses or augmented reality lenses,
wherein said imaging unit is configured to capture video data of a medication and wherein said display is configured to display said captured video data in real time.

16. The medication management method of claim 13, wherein capturing images comprises capturing video data of a medication, and wherein said displaying comprises displaying said captured video data in real time.

17. The medication management method of claim 13, further comprising identifying the characteristic features according to one or any combination of size, color, shape, logo or inscription, of the medication and identifying the medication based on said identified characteristic features and said medication database containing a plurality of medications, their characteristic features and medication description, in particular active components, interactions, side effects and intake information.

18. The medication management method of claim 13, further comprising contacting one or more externally stored medication databases, in particular via a network such as a computer network or a communications network.

19. The medication management method of claim 13, further comprising displaying said overlaid medication information as text or color indication overlaid to the displayed image.

20. The medication management method of claim 13, further comprising displaying a link or button for use by a user to obtain additional information about the displayed medication.

* * * * *